US008616205B2

(12) United States Patent
Tobias et al.

(10) Patent No.: US 8,616,205 B2
(45) Date of Patent: Dec. 31, 2013

(54) RESPIRATOR WITH END-OF-SERVICE-LIFE DETECTION (75) Inventors: Peter Tobias, Minneapolis, MN (US); Brian Krafthefer, Stillwater, MN (US)

(73) Assignee: Honeywell International Inc., Morristown, NJ (US)

( * ) Notice: Subject to any disclaimer, the term of this patent is extended or adjusted under 35 U.S.C. 154(b) by 404 days.

(21) Appl. No.: 12/899,075

(22) Filed: Oct. 6, 2010

(65) Prior Publication Data
US 2012/0085349 A1    Apr. 12, 2012

(51) Int. Cl.
*A62B 7/10*    (2006.01)
*A62B 19/00*   (2006.01)
*A62B 23/02*   (2006.01)
*F16K 31/02*   (2006.01)
*B01D 53/02*   (2006.01)
*B01D 53/30*   (2006.01)

(52) U.S. Cl.
USPC ............ 128/204.22; 128/201.25; 128/205.12; 96/111; 96/117.5

(58) Field of Classification Search
USPC ............ 128/201.25, 204.18, 204.21, 204.22, 128/205.12, 205.25, 205.27–205.29, 128/206.12, 205.23; 95/11; 96/111, 117, 96/117.5, 121, 133; 55/DIG. 33, DIG. 35
See application file for complete search history.

(56) References Cited

U.S. PATENT DOCUMENTS

| | | | |
|---|---|---|---|
| 4,512,191 A | 4/1985 | Sexton | |
| 4,873,970 A | 10/1989 | Freidank et al. | |
| 5,003,985 A | 4/1991 | White et al. | |
| 5,659,296 A | 8/1997 | Debe et al. | |
| 5,950,621 A | 9/1999 | Klockseth et al. | |
| 6,040,777 A | 3/2000 | Ammann et al. | |
| 6,497,756 B1 | 12/2002 | Curado et al. | |
| 7,042,346 B2 | 5/2006 | Paulsen | |
| 7,148,806 B2 | 12/2006 | Anttila et al. | |
| 7,201,036 B2 * | 4/2007 | Custer et al. | ............ 73/31.02 |
| 7,442,237 B1 | 10/2008 | Gardner | |
| 7,537,648 B1 | 5/2009 | Karwacki et al. | |
| 7,625,760 B2 | 12/2009 | Kitaguchi et al. | |
| 7,638,042 B2 | 12/2009 | Astle et al. | |
| 7,703,455 B2 | 4/2010 | Bunke et al. | |
| 7,736,495 B2 | 6/2010 | Ikeyama et al. | |
| 7,748,380 B1 * | 7/2010 | Phifer et al. | ............ 128/201.25 |
| 7,761,188 B2 | 7/2010 | Palmerton et al. | |
| 2009/0288561 A1 | 11/2009 | Palmerton et al. | |
| 2010/0153023 A1 | 6/2010 | Parham et al. | |

FOREIGN PATENT DOCUMENTS

WO    WO 2009029326    3/2009

\* cited by examiner

*Primary Examiner* — Jackie Ho
*Assistant Examiner* — Mark K Han
(74) *Attorney, Agent, or Firm* — Seager Tufte & Wickhem LLC.

(57) ABSTRACT

The present disclosure relates to methods and apparatus for detecting when respiratory cartridges of a respirator have reached their end-of-service-life. In some instances, two or more respiratory cartridges are removably connectable to a respirator housing, where each of the two or more respiratory cartridges receives ambient air and deliver cleaned air to the respirator housing. One of the respiratory cartridges may be configured to have a lower adsorption capacity than the remaining respirator cartridges. A gas sensor may be situated downstream of the reduced capacity respirator cartridge, and may detect an increased concentration of the targeted gas in the cleaned air delivered by the reduced capacity respiratory cartridge. When detected, an end-of-service-life indication may be provided to the user.

18 Claims, 9 Drawing Sheets

Table of maximum value for (a/b) in dependence of p and of (Am/Bm)

| p = T2 / (T1 + T2) | Am/Bm =1 | Am/Bm =2 | Am/Bm =3 | Am/Bm =5 | comments |
|---|---|---|---|---|---|
| 0 | 1.00 | 2.00 | 3.00 | 5.00 | all cartridges filled at same time, no prior warning |
| 0.1 | 0.80 | 1.70 | 2.60 | 4.40 | NIOSH minimum demand |
| 0.2 | 0.60 | 1.40 | 2.20 | 3.80 | reasonable safety margins (cartridges have variances) |
| 0.33 | 0.34 | 1.01 | 1.68 | 3.02 | |
| 0.5 | 0.00 | 0.50 | 1.00 | 2.00 | large safety margin, impossible at Am/Bm=1 |

Use six-sigma process to assure NIOSH compliance.

FIG. 9

RESPIRATOR WITH END-OF-SERVICE-LIFE DETECTION

BACKGROUND

The present disclosure relates generally to air purifying respirators having one or more replaceable respiratory cartridges, and more particularly, to methods and apparatus for detecting when the respiratory cartridges have reached their end-of-service-life.

SUMMARY

The present disclosure relates generally to air purifying respirators having one or more replaceable respiratory cartridges, and more particularly, to methods and apparatus for detecting when the respiratory cartridges have reached their end-of-service-life. In one illustrative instance, a respirator may include a respirator housing for providing cleaned air to a user. Two or more respiratory cartridges are removably connectable to the respirator housing, where each of the two or more respiratory cartridges receives ambient air and deliver cleaned air to the respirator housing.

One of the respiratory cartridges may be configured to have a lower adsorption capacity than the remaining respirator cartridges. A gas sensor may be situated downstream of the reduced capacity respirator cartridge, and may detect an increased concentration of the targeted gas in the cleaned air delivered by the reduced capacity respiratory cartridge. This may provide an early warning of when the remaining respirator cartridges are about to reach their end of life. A controller may issue an end-of-service-life indication to the user, indicating that all respirator cartridges should be changed.

DESCRIPTION

Many modern respirators appear to have no indicator when a breakthrough of harmful gases occurs in their cartridges, which would represent the end-of-service-life of the cartridges. In the past, a few cartridges have had a coarse colorimetric indicator to indicate a breakthrough of some special gases, but many of these cartridges are no longer on the market. In many cases, the user simply has to rely on making conservative estimates from data in tabular form as to when their cartridges will reached their end-of-service-life, which often leads to disposing of cartridges that have much remaining life. This often premature changing of cartridges increases the overall costs of using cartridges, and can reduce productivity.

For the next generation PAPR (powered, air purifying respirators), an end-of-service-life indicator (ESLI) may be used to detect breakthrough of harmful gas and then warn the user. For increased market penetration, the end-of-service-life indicator (ESLI) should: have a relatively low cartridge cost, particularly since the cartridges must be routinely replaced during use of the powered air purifying respirator; and produce a reliable and accurate warning before 90 percent of the useful life of the cartridge is gone, which is a regulatory requirement from the National Institute for Occupational Safety and Health (NIOSH). In many cases, the harmful gas should not exceed the exposure limits at the user during the useful life of the cartridge.

One way of adding an ESLI to a respirator is to mount a gas sensor inside one or more of the cartridges, sometimes with an absorbent downstream of the gas sensor. The gas sensor could then be used to give a warning upon detection of the targeted harmful gas. This approach, however, may significantly increase cartridge costs, and may complicate communication with the sensor. Additionally, one would likely need to have a power supply such as either a disposable battery in the cartridge (costly) or additional wiring in the thread from the respirator housing.

Another way of adding an ESLI is to mount a gas sensor within the respirator housing itself. For example, in a PAPR, one may mount an ESLI sensor in a respirator housing, where the sensor can be used multiple times (i.e. for multiple cartridges) and may tap into power that is supplied for the pump and/or other components. When such power is readily available, there are many robust commercial gas sensors available with known reliability characteristics and sensitivities. With the sensor position in the respirator housing, as opposed to the cartridges, the sensor may more easily communicate with a local microprocessor or microcontroller, if desired. The size limit for sensors in this configuration may also be larger than for sensors in a cartridge, as is the power limit, compared to battery driven sensors. If size and power have larger limits, there may be more sensors available that can measure concentrations of a volatile organic compound (VOC) and/or other gases in the lower ppm range.

To protect the user from exposure to harmful gas concentration, one may modify one or more of the cartridges using the following configuration. From the multiple cartridges used in a typical PAPR, one cartridge may be configured to have a lower adsorption capacity for the targeted gas(es). This may help ensure that this cartridge will be the first to breakthrough. One may place a gas sensor at the outflow of this cartridge, and sometimes inside the PAPR respirator housing. When the sensor detects a gas breakthrough, an optional valve may be provided to stop any additional flow through the selected cartridge. The flow through the remaining cartridges may thus be increased, to keep the total flow relatively constant for the user. At the same time, the system may warn the user and ask the user to replace all cartridges with new ones at this time. In some cases, at the time of sensor alarm, the user may be exposed to some elevated concentrations of the targeted gas(es) for a short time, but the concentrations would preferably remain below the short term exposure limit.

A PAPR may have enough power (currently 4-5 watts) to provide a small amount of power to the gas sensor(s). It can be estimated that an addition of the selected gas sensors and optional valve may increase the cost of the PAPR system by, for example, 20-40 percent. The cost of a cartridge set may remain relatively low because the gas sensor(s) need not be replaced when the cartridge set is replaced. The maintenance intervals for the sensor could coincide with the maintenance of the PAPR housing and its pump.

In one instance, and as described above, one cartridge may be made deliberately smaller or otherwise made to have a lower adsorption capacity for the targeted gas(es) than the other cartridge(s) of the PAPR. An ESLI sensor and an optional valve may be placed downstream of the smaller cartridge. In other instances, one of the cartridges may be effectively split into two separate cartridges, with one of the split cartridges positioned downstream of the other, and with an ESLI sensor positioned between the two split cartridges.

In the presence of a PAPR herein, one may note several items. One is that the users may mount multiple new cartridges of one cartridge set, but one of the cartridges, cartridges B (cartridge 18 in FIG. 2), would not be interchangeable with the other cartridges. In one example, the thread 36 of cartridge 18 may have a widely different thread size, to help prevent mounting the cartridges in the wrong place on the PAPR housing. Only the other cartridges, A1 (cartridge 21 in FIG. 2), A2 (cartridge 22 in FIG. 2), and so forth, would be interchangeable.

In some cases, one may mount a tube inside the respirator housing, fitted on the outflow of the cartridge 18 that has a reduced absorption capacity. The tube may be equipped with a gas sensor for the targeted gas, and may also include a two-way valve of which both can be connected to the PAPR's microcontroller.

The respirator housing may have a microcontroller to read the sensor signal, control the pump, control the valve, send warnings to the user, calculating noise cancellation, communicating with a base station, and/or perform other control and/or communication functions, as desired.

In one or more illustrative examples, as described herein, or in other respirator configurations, features and/or structure of a respirator housing may be integrated into a corresponding mask. In such cases, the terms "respirator housing" and "mask" may be used interchangeably to refer to same item in some of the examples disclosed herein, and other configurations. Also in some examples and other configurations, certain features and/or structure of the pump and its respective housing may similarly be integrated, in part or in whole, into the mask.

Figure 1:
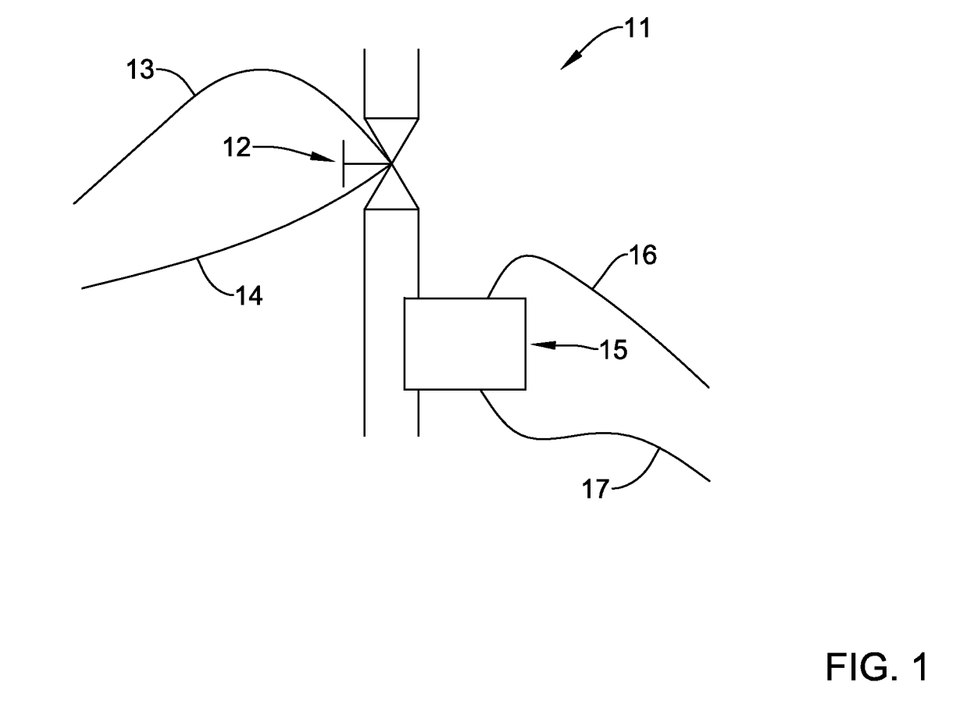
FIG. 1 is a diagram of a tube which may be added inside a PAPR respirator housing fitted to an outflow of a cartridge.
Figure 2:
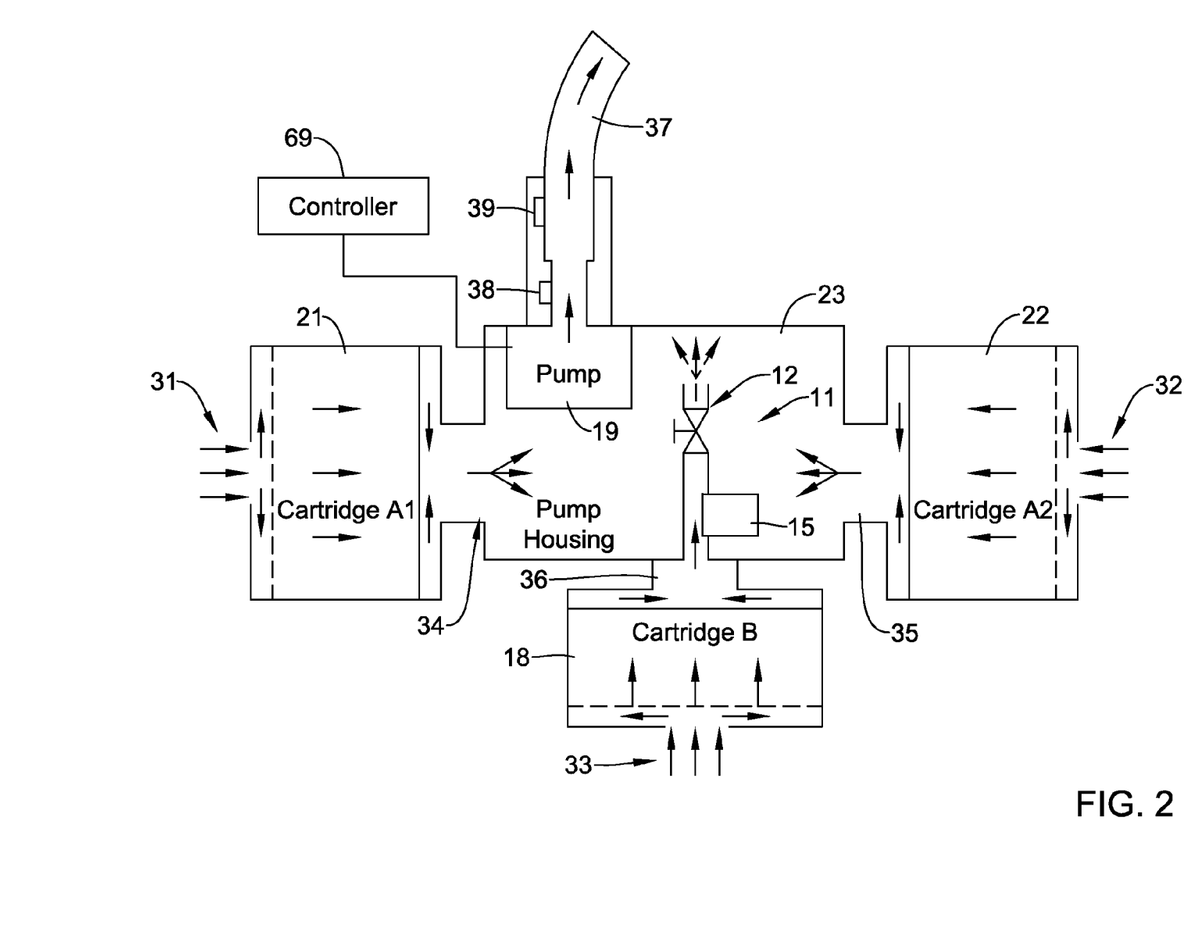
FIG. 2 is a diagram of an overall view of a system incorporating an arrangement of FIG. 1.

Turning now specifically to the Figures, where FIG. 1 shows a tube 11 which may be added inside a PAPR respirator housing fitted to an outflow of a cartridge 18 of FIG. 2. FIG. 2 is a diagram of an illustrative PAPR system. In FIG. 1, tube 11 is shown having a two-way valve 12 with an electrical connection 13 and 14 for actuation. There may also be a gas sensor 15 probing the interior of tube 11, with electrical connections 16 and 17. The gas sensor 15 may be used for detecting a breakthrough of cartridge 18, which as indicated above, may have a reduced absorption capacity than cartridges A1 21 and A2 22. Tube 11 may be added to a respirator housing 23, if desired.

A breakthrough from an input flow 33 of harmful gases to an output at thread 36 should occur first at cartridge 18. The gas sensor 15 positioned downstream of cartridge 18 may detect the breakthrough and provide a warning to the user to exchange the whole set of cartridges 18, 21 and 22. At the same time, the valve 12 may stop further flow through cartridge 18, and the pump 19 may increase the flow through cartridge 21, cartridge 22, and so on, to maintain a relatively constant flow to the user.

A question may be how much unfilled absorbent is left in the cartridges 21, 22, and the like, when the breakthrough of cartridge 18 occurs. Multiple cartridges in parallel are not necessarily filled at exactly the same rate, but the deviations between them may be normally small, typically less than 3 percent. Therefore, monitoring only one of the multiple cartridges 18, 21 and 22, is believed to be sufficient to give a warning to the user that it is timely for all cartridges to be changed.

Rather than placing the gas sensor 15 upstream of the valve 12, it is contemplated that the gas sensor 15 may be placed downstream from valve 12, as long as its ambient is predominantly gas from cartridge 18 when the gas flows through cartridge 18. After valve 12 is closed, the gas sensor downstream of the valve 12 could sense gas from the cartridges 21, 22, and so on. If one of those cartridges has a breakthrough, such a gas sensor 15 downstream of the valve 12 could give a warning to the user to immediately leave the area of harmful gas.

One may need to choose right materials for the added tube and components, to avoid gas absorption inside respirator housing 23, otherwise the materials could outgas after the cartridge set is replaced, which could trigger an alarm or do other unwanted things.

One may also make all threads for cartridges 18, 21, 22 the same and allow the cartridge 18 to be mounted on any of the three or more threads. However, one may need to equip every outflow with a tube 11 having a sensor 15 and a valve 12, which may increase costs.

In the PAPR system of FIG. 2, and around the time of the warning, the user may be exposed to some elevated gas concentrations for a short period of time, but the concentrations would likely remain below the short term exposure limit.

There may be an air flow input 31 for cartridge 21, an air flow input 32 for cartridge 22, and an air flow input 33 for cartridge 18. There may be a thread 34 for cartridge 21, a thread 35 for cartridge 22 and a thread 36 for cartridge 18. While threads are mentioned here for connecting the cartridges to the respirator housing 23, it is contemplated that any suitable connector may be used, such as a bayonet style connection, a clamp type connection, or any other suitable connection as desired.

During use, air may be pumped out through an exit tube 37 by pump 19. In some cases, there may be a microphone 38 for noise monitoring in exit tube 37. Also, inside exit tube 37 may be a loudspeaker 39, which may provide an audible alarm with detailed warnings, and in some cases, for noise cancellation.

Figure 3:
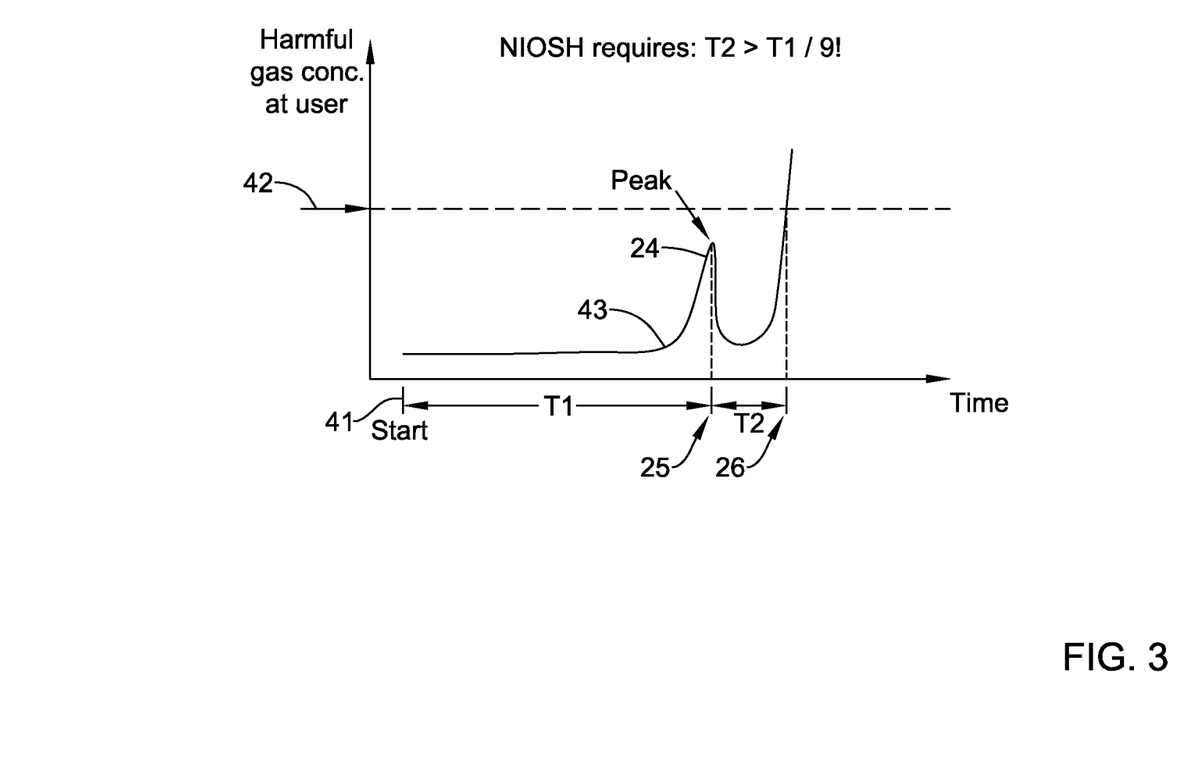
FIG. 3 is a diagram of a graph showing harmful gas concentration at a user over time.

FIG. 3 is a graph showing harmful gas concentration at the user over time for the system shown in FIG. 2. The graph has a curve 43 starting at time 41 and running for a period T1 of time to time 25 where a peak 24 is noted. From time 25 to time 26 is a period T2 of time. At time 26, the gas concentration is shown to suddenly increase. The National Institute for Occupational Safety and Health (NIOSH) appears to have a requirement that T2>(T1/9). Level 42 may be a threshold of harmful gas concentration; in other words, level 42 may be regarded as a short term exposure limit. Time 25 is when a breakthrough may be detected in cartridge 18. Time 26 is when a cartridge 21 or cartridge 22 breakthrough may be detected. During time T2, the user may exit the contaminated environment and change the cartridge set without haste.

Gas concentration at a user over time may be described as follows. First, a gas may stream through all cartridges, with the flows "a" (i.e., total flow through cartridges 21, 22, and so on) and "b" (i.e., flow through cartridge 18), where the total flow=a+b.

Second, after a time 25, T1, cartridge 18 may be filled, and the target gas may breakthrough cartridge 18. The sensor 15 may give a warning to exchange the cartridge set. In some cases, a relatively small concentration of target gas may reach the user at this point (i.e., peak 24). Third, valve 12 may be closed and only cartridges 21, 22, and so on, continue to provide purified air for the user. Their added flow rates may be increased, from "a" to "a+b", to maintain a relatively constant total flow. Cartridges 21, 22, and so on, may now be filling slightly faster with target gas than when gas also flowed through cartridge 18.

Fourth, after another time 26, T2, the cartridges 21, 22, and so on, may become filled, and the target gas would have reached the user with an ambient concentration if the cartridges had not yet been exchanged by the user.

Figure 4:
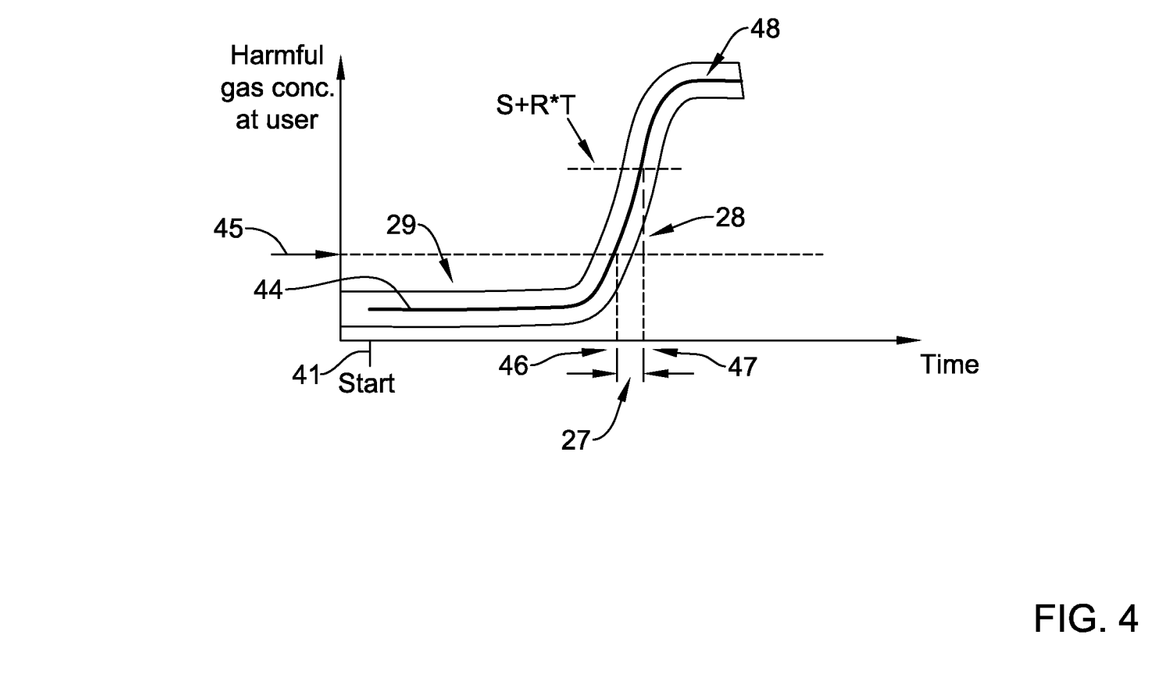
FIG. 4 is a diagram of a graph illustrating a cartridge breakthrough.

The height of the indicated peak 24, P, should be below the acceptable short-term exposure limit. With reference to FIG. 4, the peak height may depend on the following various parameters: a) alarm threshold of the sensor 15, S (not too low so as not to be triggered by noise); b) response time 27 of sensor 15, T; c) increase of gas concentration at the sensor 15 after breakthrough, R, which shows slope 28 of gas increase after cartridge 18 breakthrough; and d) the ratio of the flows (b/a) cartridge 18 flow/cartridges 21 and 22 flow.

Relative to FIG. 4, the black curve 44 may start at time 41. Level 45 shows S=alarm threshold. A cartridge 18 breakthrough may occur at time 46. The breakthrough of cartridge 18 may be detected at time 47. The time difference 27 between occurrence and detection may be regarded as T=sensor response time. From time 46 to 47, an R=slope 28 of gas increase after the breakthrough. At the top of the slope on curve 44 at time 47, S+R*T may be noted. The top 48 of curve 44, where the concentration of gas at the sensor 15 stops increasing, may be indicative that the valve is closed and the flow through cartridge 18 stops.

The black curve 44 shows the expected sensor signal over time, and the grey envelope 29 indicates the uncertainty of the sensor signal. The following items may be noted.

Peak height $P=(S+R*T)*b/(a+b)$=about=$(S+R*T)*(b/a)$ if $(b/a)\ll 1$.

R may depend on the absorbent, and the kind of gas and its ambient concentration (the present ESLI approach may have little influence on those).

S and T may depend on the sensor type; both should be small in this configuration.

(b/a) may depend on the choice of dimensions of the system. A low (b/a) may bring down the peak height.

One should choose S, T, and (b/a) carefully and use a limit for R. One suitable upper limit for R may be the measured R value for the considered cartridge type using the concentration of the harmful gas that is immediately dangerous to life, above which the air purifying respirator cannot be used.

On the other hand, the ratio (b/a) should not be designed too small. Otherwise the cartridge 18 may lose its function as being the cartridge with the first breakthrough. The lower bound of (b/a) (or upper bound for (a/b)) may depend on the ratio of the capacity of the cartridges and on the required safety margin. For example, for a constant concentration of the harmful gas in the ambient, a ratio of capacities of 5 and a desired time before breakthrough of 33 percent, one may find that (a/b) should be below 3.02 or (b/a) should be above 0.33.

Figure 5:
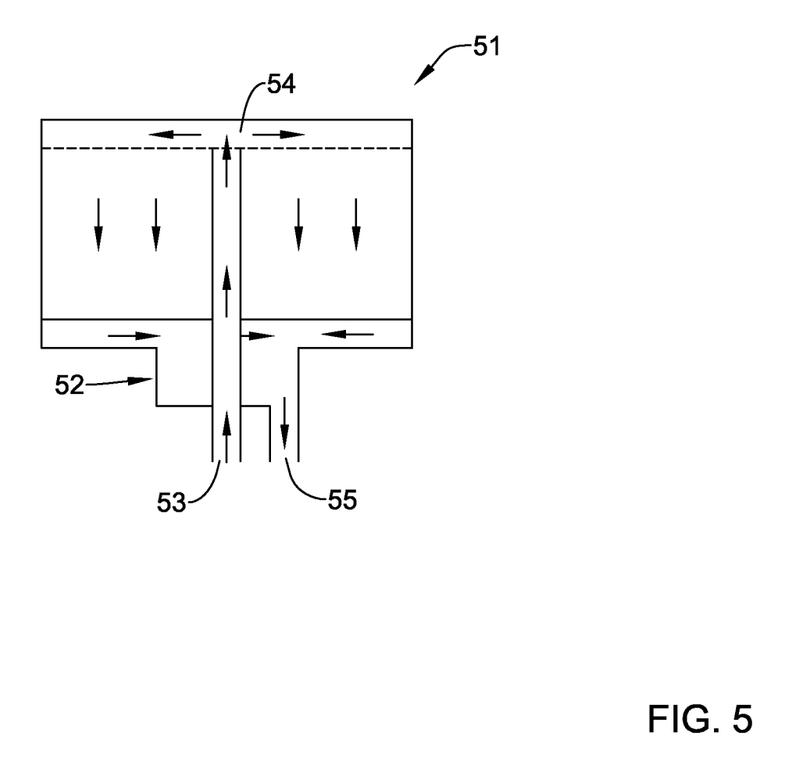
FIG. 5 is a diagram of an optional cartridge and its flow pattern.

FIG. 5 is a diagram of an optional (e.g. fourth) cartridge B2 (i.e., cartridge 51) with a thread 52. A flow may enter at entry 53, and do a U-turn at location 54 and exit cartridge 51 at exit 55. If the peak of gas exposure around the time of the warning is unacceptable, the fourth cartridge 51 may be placed downstream of the gas sensor 15, and would absorb any harmful gas that breaks through cartridge 18.

It may be desirable that all cartridges be mounted in the same way on the pump house 23, to make the exchange easier for the user. Cartridges 21, 22, and so on, and cartridge 18 may receive their incoming air from the ambient environment and may look similar to today's cartridges. Cartridge 51, however, may receive its incoming air from the respirator housing 23 and give its outgoing air back into the respirator housing 23. A cartridge 51 construction may let the gas make a U-turn in the cartridge and still separate the incoming and outgoing gas streams reliably from each other, as shown on FIG. 5.

In some instances, both cartridges 18 and 51 would be screwed into their specific positions and have specific thread sizes so as not to permit them to be interchangeable with the other cartridges 21, 22, and so on.

If the cartridge 51 is large enough, the valve 12 may not be needed and may be optional. If valve 12 is eliminated, harmful gas from cartridge 18 would be absorbed in cartridge 51, between the times of the warning and the exchange of all of the cartridges with replacement cartridges.

Figure 6:
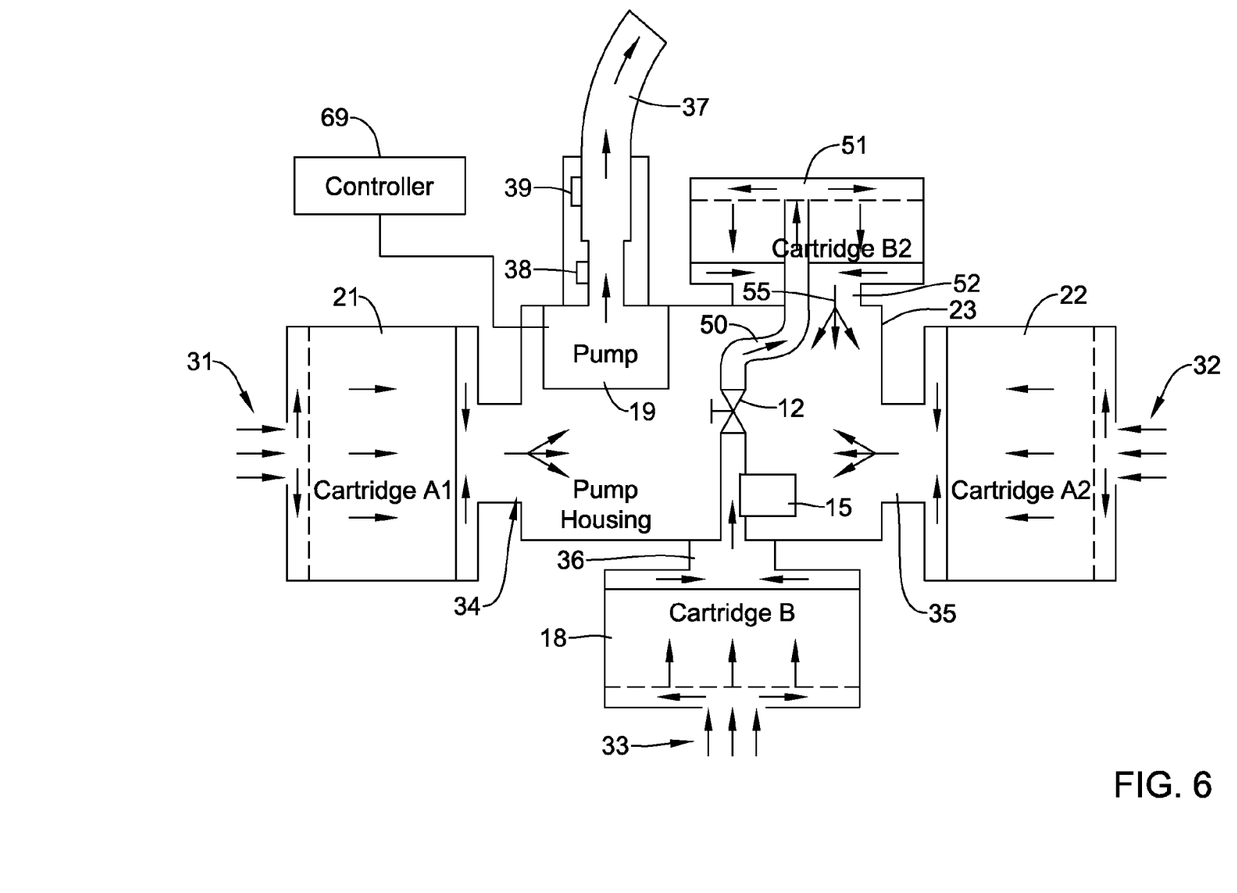
FIG. 6 is a diagram similar to FIG. 2 except that another cartridge is added with its input connected to an output of a valve via a conveyance.

FIG. 6 appears similar to FIG. 2 except that the fourth cartridge 51 is shown with its input 53 connected to an output of valve 12 via a conveyance 50. The output 55 of cartridge 51 may have a flow into housing 23.

An option of the present approach may incorporate a PAPR with three cartridges 18, 21 and 22, a valve 12, and a simple cap to cover the thread port for the fourth cartridge 51. Another option may be to exchange the cap with the fourth cartridge 51 to eliminate the gas peak, when desired.

Figure 7:
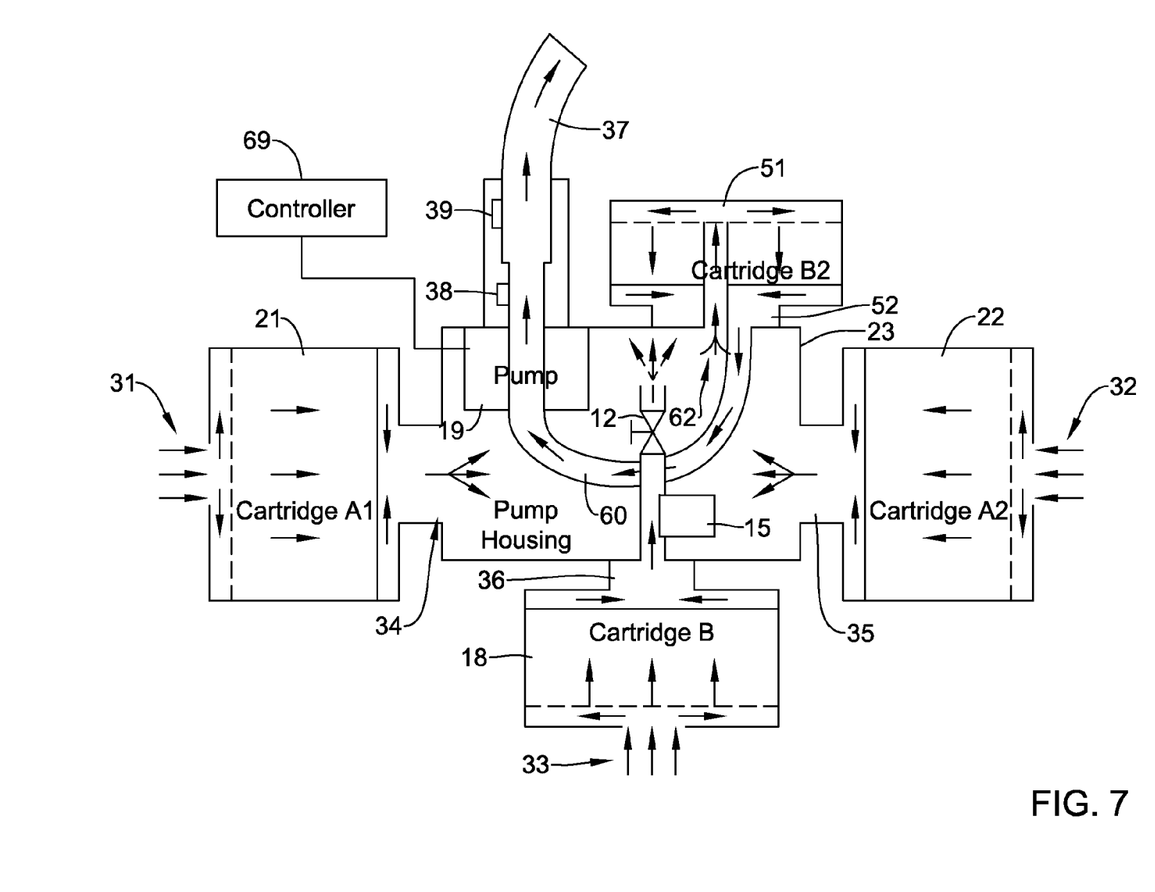
FIG. 7 is a diagram similar to that of FIG. 6 except in this illustrative example the optional cartridge is downstream from all of the other cartridges rather than just one of them.

FIG. 7 is a diagram similar to that of FIG. 6 except in this illustrative example the optional cartridge 51 may be downstream from cartridges 21, 22 and 18 rather than just from cartridge 18. Outputs from these cartridges may go to an input 62 of the U-turn cartridge 51, go through cartridge 51 and then to an output connected to a conveyance 60 that goes to pump 19 for exhaust though exit tube 37.

Figure 8:
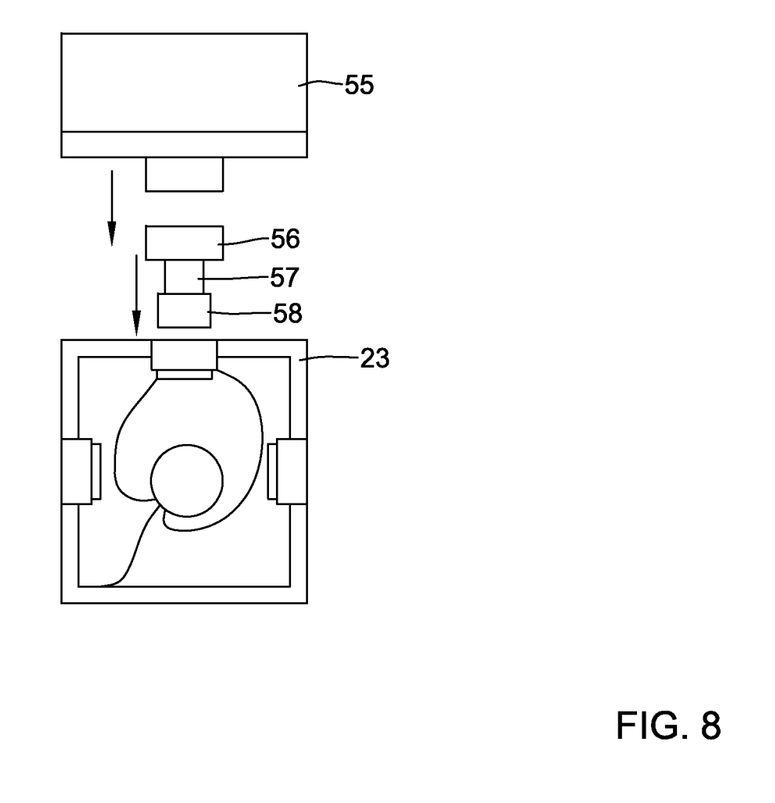
FIG. 8 is a diagram of an alternative to the optional cartridge in FIG. 5.

Another way to have the function of the fourth cartridge would be to add an adapter to cartridge 18 that contains a location for a sensor 15 and a downstream absorbent of cartridge 51. FIG. 8 is a diagram of one such adapter. In FIG. 8, there is shown a smaller cartridge 55 (similar to cartridge 18 discussed above), which may hook into a threaded holder 56. A sensor 57 and a buffer cartridge 58, in that order, may fit into the holder 56, and the holder 56 may be connected to the housing 23.

In some instances, there may be an audio alarm for the PAPR provided inside the tube to the mask or hood for several reasons. If PAPR is carried on the back where a wearer could not see an LED reliably, acoustic (and/or vibrational) signals could still be sensed by the user. The acoustic signal may also be used to ask the user to look onto a display. An audio signal inside the tube 37 may be less weakened on its way to the user's ear and, therefore, be more reliably received in a noisy environment. It is contemplated that multiple alarm types may be incorporated, e.g., audio, visual, vibrational, and so forth.

Another goal may be to help reduce the pump noise to the user. Examples may incorporate using a muffler between pump 19 and the user, using an absorbent between the pump and user as the muffler and as an absorbent to prevent gas coming to the user especially after the smaller cartridge 18 has a breakthrough, and/or measuring the pump noise with a nearby microphone and canceling the noise with the loudspeaker. In some cases, sound from the loudspeaker may be provided in opposite phase to the pump noise so as to cancel out most of the pump noise before reaching the hood or mask. If a loudspeaker is needed anyway for warnings by the ESLI system, then a loudspeaker inside the tube may also be used for active noise cancellation. To help control these and other functions of the PAPR, a microcontroller 69 may be placed in or connected to respirator housing 23.

Another approach may be to implement an end-of-service-life indicator for the dust filters. A comparison of pump power and measured pressure drop over the cartridges or measured flow in the tube may give a measure of the clogging of the dust filter. However, the comparison of pump power and sensor data may require extra circuitry, such as that of microcontroller 69. The microcontroller may be used for many purposes, like canceling noise, generating appropriate audio alarms, and controlling the ESLI.

A needed minimum ratio of flow (b/a) may be calculated herein. Various parameters may be indicated with designations as in the following.

Capacity of cartridges 21, 22, and so on=Am
Flow through cartridges 21, 22, and so on=a
Capacity of cartridge 18=Bm
Flow through cartridge 18=b
T1: time from start until flow through cartridge 18 is stopped
T2: time from stopping flow through cartridge 18 to breakthrough of cartridges 21, 22, and so on
For same absorbent and gas, one may assume:

$$Time * Flow\_X = Load\_X(time)$$

When Load (time) reaches Capacity, then the cartridge in question is filled enough to no longer protect the user sufficiently $$(T1 - \text{response time}) * b = Bm = \text{about} = T1 * b$$

and $$T1 * a = Load\_A(T1)$$

$$T2*(a+b) + Load A(T1) = Am = T2*(a+b) + T1*a$$

A designer might choose different percentages, p, of T2 on the total time T1+T2:

$$T2 = p*(T1+T2) => T2 = T1*p/(1-p)$$

$$Am = T2*(a+b) + T1*a = T1*(a*p)/(1-p) + b*p/(1-p) + a)$$
$$= T1*(a/(1-p) + b*p/(1-p))$$

$$Bm = T1*b => (Am/Bm) = (a/b)/(1-p) + p/(1-p) => (a/b) = (1-p)*(Am/Bm) - p$$

(b/a) may have a lower limit above which the cartridge 18 cannot function as a warning cartridge anymore where each breakthrough occurs. (a/b) consequently may have an upper limit, which should not be exceeded.

Figure 9:
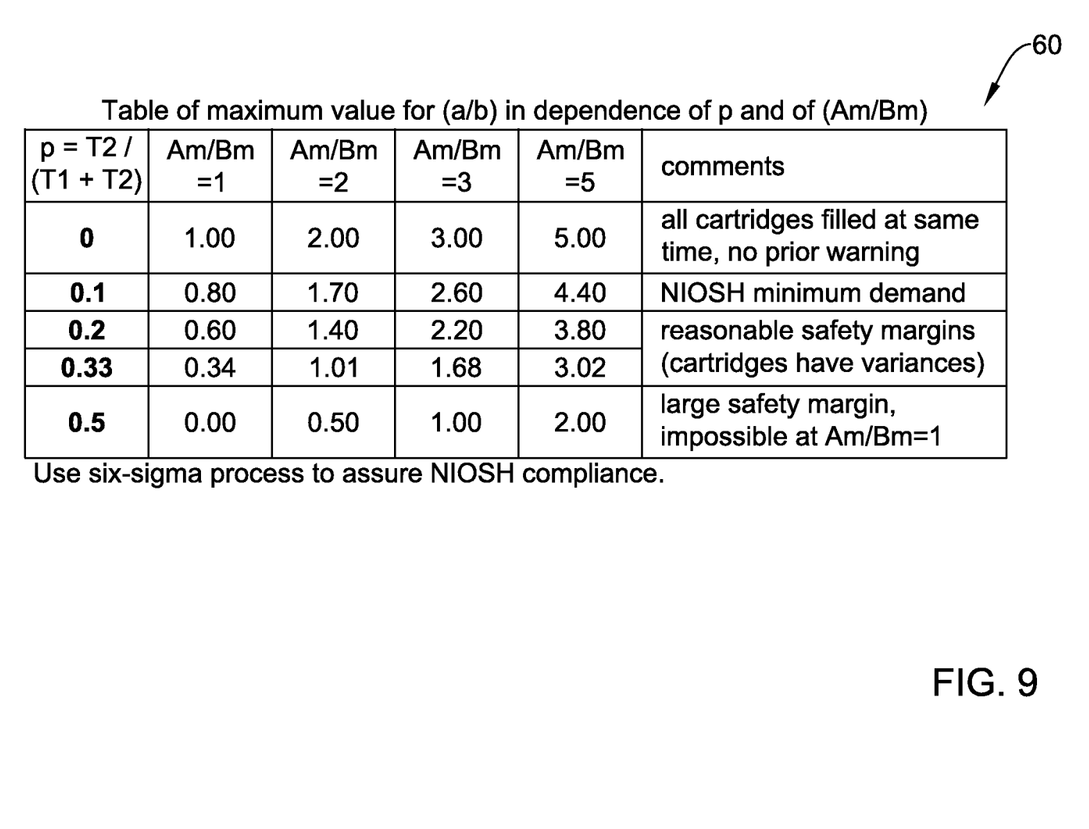
FIG. 9 is a diagram of a table showing illustrative maximum values for a flow ratio of cartridges in dependence of times and cartridge capacities in one illustrative arrangement.

A table 61 of illustrative maximum values for (a/b) in dependence of p and of (Am/Bm) is shown in FIG. 9. A six-sigma process may be used to assure NIOSH compliance when determining the values in the table, by relating the gas absorption capacities and the flow resistances of the various cartridges to each other.

In the present specification, some of the matter may be of a hypothetical or prophetic nature although stated in another manner or tense.

Although the present system has been described with respect to at least one illustrative example, many variations and modifications will become apparent to those skilled in the art upon reading the specification. It is therefore the intention that the appended claims be interpreted as broadly as possible in view of the prior art to include all such variations and modifications.

What is claimed is:

1. A respirator comprising:
   a respirator housing for providing cleaned air to a user;
   two or more respiratory cartridges removably connectable to the respirator housing, each of the two or more respiratory cartridges receiving ambient air and delivering cleaned air to the respirator housing;
   a first one of the two or more respiratory cartridges having a lower adsorption capacity for a targeted gas than at least one other of the two or more respiratory cartridges;
   a gas sensor positioned downstream of the first one of the two or more respiratory cartridges for detecting an increased concentration of the targeted gas in the cleaned air delivered by the first one of the two or more respiratory cartridges to the respirator housing; and
   a second one of the two or more respiratory cartridges, wherein a flow through the second one of the two or more cartridges increases when the gas sensor detects an increased concentration of the targeted gas.

2. The respirator of claim 1 further comprising a pump for pumping cleaned air from the respirator housing to the user.

3. The respirator of claim 1 further comprising a controller coupled to the gas sensor, wherein the controller issues an end-of-service-life indication to the user when the gas sensor detects the increased concentration of the target gas.

4. The respirator of claim 1 further comprising a tube fluidly interposed between an outlet of the first one of the two or more respiratory cartridges and the respirator housing, and wherein the gas sensor is exposed to an interior of the tube.

5. The respirator of claim 4, further comprising a valve for selectively stopping a flow through the first one of the two or more respiratory cartridges.

6. The respirator of claim 5 further comprising a controller coupled to the gas sensor and the valve, wherein the controller closes the valve when the gas sensor detects an increased concentration of the targeted gas in the tube.

7. The respirator of claim 4 further comprising a third one of the two or more respiratory cartridges that has an inlet in fluid communication with the tube, and an outlet in fluid communication with the respirator housing.

8. The respirator of claim 7, wherein the flow through the third one of the two or more respiratory cartridges experiences a U-turn.

9. The respirator of claim 1, further comprising a third one of the two or more respiratory cartridges that has an inlet in fluid communication with the respirator housing and an outlet adapted to be in fluid communication with a gas stream flowing to the user of the respirator.

10. The respirator of claim 1, further comprising an adapter situated between an outlet of the first one of the two or more respiratory cartridges and the respirator housing, wherein the adapter contains the gas sensor and a downstream absorbent.

11. A respirator comprising:
    a respirator housing for providing cleaned air to a user;
    a pump for pumping cleaned air from the respirator housing to the user;
    a first respiratory cartridge connectable to the respirator housing, the first respiratory cartridge receiving ambient air and delivering cleaned air to the respirator housing;
    a second respiratory cartridge connectable to the respirator housing, the second respiratory cartridge receiving ambient air and delivering cleaned air to the respirator housing;

a third respiratory cartridge connectable to the respirator housing, the third respiratory cartridge receiving ambient air and delivering cleaned air to the respirator housing;

the first respiratory cartridge having a lower adsorption capacity for a targeted gas than the second respiratory cartridge and the third respiratory cartridge;

a tube fluidly interposed between an outlet of the first respiratory cartridge and the respirator housing;

a gas sensor exposed to an interior of the tube;

a valve for selectively closing off the tube; and a controller coupled to the gas sensor and the valve, wherein the controller closes the valve when the gas sensor detects an increased concentration of the targeted gas in the tube, the controller also issues an end-of-service-life indication to the user when the gas sensor detects an increased concentration of the targeted gas in the tube; and wherein a flow through the second respiratory cartridge and/or the third respiratory cartridge is increased when the gas sensor detects an increased concentration of the targeted gas in the tube.

12. The respirator of claim 11 further comprising a fourth respiratory cartridge that has an inlet in fluid communication with the tube, and an outlet in fluid communication with the respirator housing.

13. The respirator of claim 12, wherein the flow through the fourth respiratory cartridge experiences a U-turn.

14. A method for providing cleaned air to a user, comprising:

passing ambient air through two or more respiratory cartridges into a respirator housing, wherein a first one of the two or more respiratory cartridges has a lower adsorption capacity for a targeted gas than at least one other of the two or more respirator cartridges;

using a gas sensor positioned downstream of the first one of the two or more respiratory cartridges to detect an increased concentration of the targeted gas in air cleaned and delivered by the first one of the two or more respiratory cartridges to the respirator housing;

detecting with the gas sensor when the first one of the two or more respiratory cartridges has a targeted gas break through;

increasing a flow rate of air through the at least one other of the two or more respiratory cartridges after the gas sensor has detected that the first one of the two or more respiratory cartridges has the targeted gas break through; and issuing an end-of-service-life indication to the user when the gas sensor has detected that the first one of the two or more respiratory cartridges has the targeted gas break through.

15. The method of claim 14, further comprising preventing air from passing from the first one of the two or more respiratory cartridges to the respirator housing when the gas sensor has detected that the first one of the two or more respiratory cartridges has the targeted gas break through.

16. The method of claim 14, further comprising replacing all of the two or more respiratory cartridges after the end-of-service-life indication is issued.

17. A respirator comprising:

a respirator housing for providing cleaned air to a user;

a first respiratory cartridge and a second respiratory cartridge removably connected to the respirator housing, the first and second respiratory cartridges receiving ambient air and delivering cleaned air to the respirator housing;

the first respiratory cartridge having a lower adsorption capacity for a targeted gas than the second respiratory cartridge;

a gas sensor positioned downstream of the first respiratory cartridge configured to detect an increased concentration of the targeted gas in the cleaned air delivered by the first respiratory cartridge to the respirator housing;

a tube fluidly interposed between an outlet of the first respiratory cartridge and the respirator housing;

a valve positioned downstream of the gas sensor for selectively closing off the tube; and wherein a flow through the second respiratory cartridge increases when the gas sensor detects an increased concentration of the targeted gas.

18. The respirator of claim 17, wherein the first respiratory cartridge has a first thread size and the second respiratory cartridge has a second thread size different than the first thread size.

* * * * *